United States Patent [19]
Pinchuk

[11] Patent Number: 5,855,598
[45] Date of Patent: *Jan. 5, 1999

[54] EXPANDABLE SUPPORTIVE BRANCHED ENDOLUMINAL GRAFTS

[75] Inventor: Leonard Pinchuk, Miami, Fla.

[73] Assignee: Corvita Corporation, Miami, Fla.

[ * ] Notice: The term of this patent shall not extend beyond the expiration date of Pat. No. 5,639,278.

[21] Appl. No.: 863,964

[22] Filed: May 27, 1997

Related U.S. Application Data

[63] Continuation-in-part of Ser. No. 558,028, Nov. 13, 1995, Pat. No. 5,632,772, and a continuation-in-part of Ser. No. 558,034, Nov. 13, 1995, Pat. No. 5,639,278, each is a continuation-in-part of Ser. No.140,245, Oct. 21, 1993, abandoned.

[51] Int. Cl.$^6$ ........................................................ A61F 2/06
[52] U.S. Cl. .................................................... 623/1
[58] Field of Search ..................... 623/1, 11, 12

[56] References Cited

U.S. PATENT DOCUMENTS

| | | | |
|---|---|---|---|
| 3,700,380 | 10/1972 | Kitrilakis | 623/1 |
| 4,173,689 | 11/1979 | Lyman et al. | 521/64 |
| 4,286,341 | 9/1981 | Greer et al. | 623/1 |
| 4,323,525 | 4/1982 | Bornat | 264/24 |
| 4,459,252 | 7/1984 | MacGregor | 264/46.9 |
| 4,475,972 | 10/1984 | Wong | 156/167 |
| 4,512,338 | 4/1985 | Balko et al. | 128/1 R |
| 4,555,771 | 11/1985 | Wallsten | 623/1 |
| 4,580,568 | 4/1986 | Gianturco | 128/345 |
| 4,604,762 | 8/1986 | Robinson | 623/1 |
| 4,712,553 | 12/1987 | MacGregor | 128/355.5 |
| 4,731,073 | 3/1988 | Robinson | 623/1 |
| 4,733,665 | 3/1988 | Palmaz | 128/343 |
| 4,738,740 | 4/1988 | Pinchuk et al. | 156/167 |
| 4,800,882 | 1/1989 | Gianturco | 128/343 |

(List continued on next page.)

FOREIGN PATENT DOCUMENTS

| | | | |
|---|---|---|---|
| 009941 | 4/1980 | European Pat. Off. . | |
| 461791 | 12/1991 | European Pat. Off. . | |
| 539237 | 4/1993 | European Pat. Off. | 623/1 |
| 551179 | 7/1993 | European Pat. Off. . | |
| 686379 | 12/1995 | European Pat. Off. . | |
| 603959 | 9/1996 | European Pat. Off. . | |
| 3918736 | 12/1990 | Germany . | |
| 1205743 | 9/1970 | United Kingdom . | |
| 2115776 | 9/1983 | United Kingdom . | |
| 2189150 | 10/1987 | United Kingdom | 623/1 |
| 9206734 | 4/1992 | WIPO . | |
| 09246 | 6/1992 | WIPO | 623/1 |
| 9401056 | 1/1994 | WIPO . | |
| 9413224 | 6/1994 | WIPO . | |
| 9513033 | 5/1995 | WIPO | 623/1 |

*Primary Examiner*—Michael J. Milano
*Attorney, Agent, or Firm*—Lockwood, Alex, Fitz-Gibbon & Cummings

[57] ABSTRACT

An endoluminal graft which is both expandable and supportive is provided in a form suitable for use in a branched body vessel location. The graft expands between a first diameter and a second, larger diameter. The support component is an expandable stent endoprosthesis. A liner is applied to the endoprosthesis in the form of a compliant wall material that is porous and biocompatible in order to allow normal cellular invasion upon implantation, without stenosis, when the expandable and supportive graft is at its second diameter. The supportive endoluminal graft is preferably provided as a plurality of components that are deployed separately at the branching body vessel location, one of which has a longitudinal seam defining leg portions within which the other components fit in a telescoping manner.

30 Claims, 6 Drawing Sheets

U.S. PATENT DOCUMENTS

| | | | |
|---|---|---|---|
| 4,816,028 | 3/1989 | Kapadia et al. | 623/1 |
| 4,820,298 | 4/1989 | Leveen et al. | 623/1 |
| 4,873,308 | 10/1989 | Coury et al. | 528/75 |
| 4,878,908 | 11/1989 | Martin et al. | 623/1 |
| 4,950,227 | 8/1990 | Savin et al. | 604/8 |
| 4,954,126 | 9/1990 | Wallsten | 600/36 |
| 4,994,071 | 2/1991 | MacGregor | 606/194 |
| 5,019,090 | 5/1991 | Pinchuk | 606/194 |
| 5,104,399 | 4/1992 | Lazarus | 623/1 |
| 5,116,360 | 5/1992 | Pinchuk et al. | 623/1 |
| 5,156,620 | 10/1992 | Pigott | 623/1 |
| 5,171,262 | 12/1992 | MacGregor | 623/1 |
| 5,195,984 | 3/1993 | Schatz | 606/195 |
| 5,236,447 | 8/1993 | Kubo et al. | 623/1 |
| 5,282,823 | 2/1994 | Schwartz et al. | 606/198 |
| 5,290,305 | 3/1994 | Inoue | 606/191 |
| 5,330,500 | 7/1994 | Song | 606/198 |
| 5,354,308 | 10/1994 | Simon et al. | 606/198 |
| 5,356,423 | 10/1994 | Tihon et al. | 606/194 |
| 5,360,443 | 11/1994 | Barone et al. | 606/191 |
| 5,385,580 | 1/1995 | Schmitt | 623/1 |
| 5,443,499 | 8/1995 | Schmitt | 623/1 |
| 5,562,724 | 10/1996 | Vorwerk | 623/1 |
| 5,632,772 | 5/1997 | Alcime et al. | 623/1 |
| 5,639,278 | 6/1997 | Dereume et al. | 623/1 |
| 5,653,747 | 8/1997 | Dereume | 623/1 |

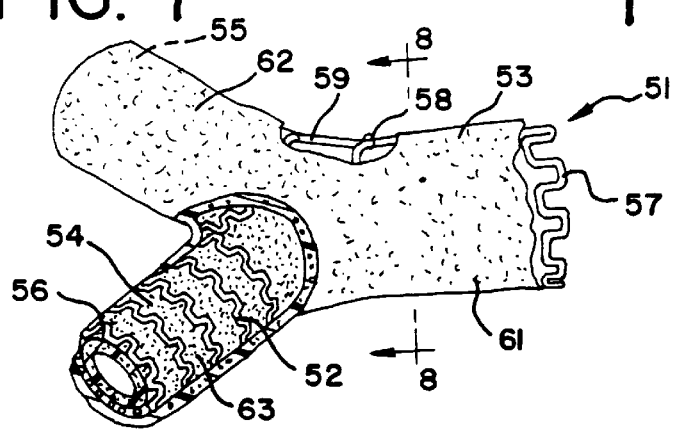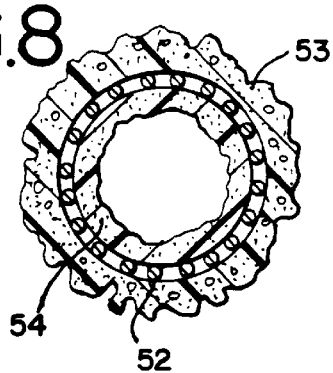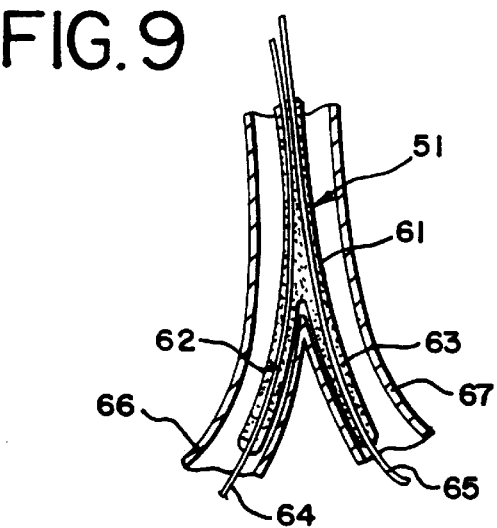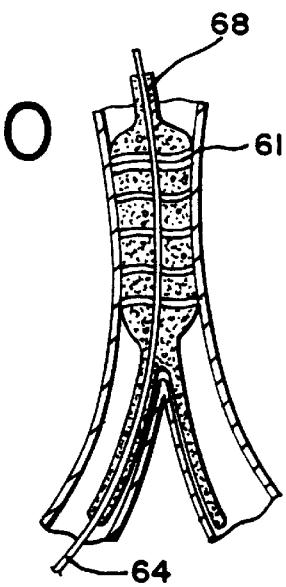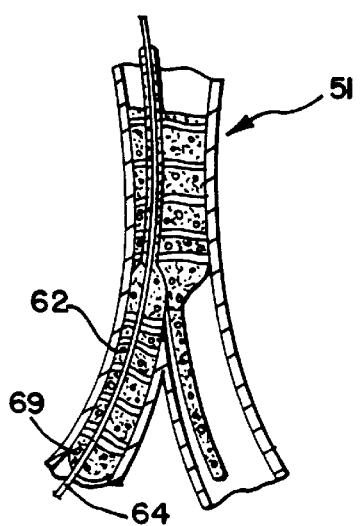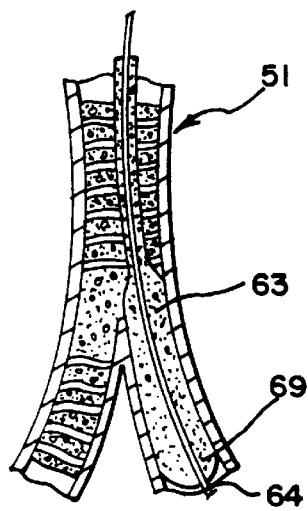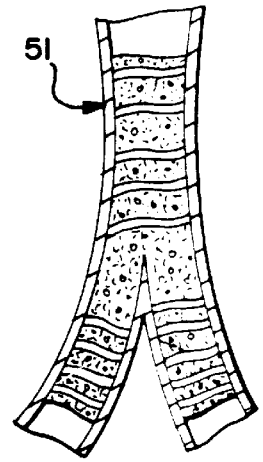

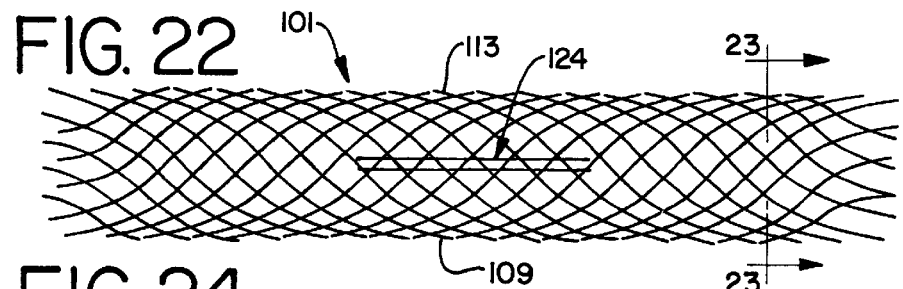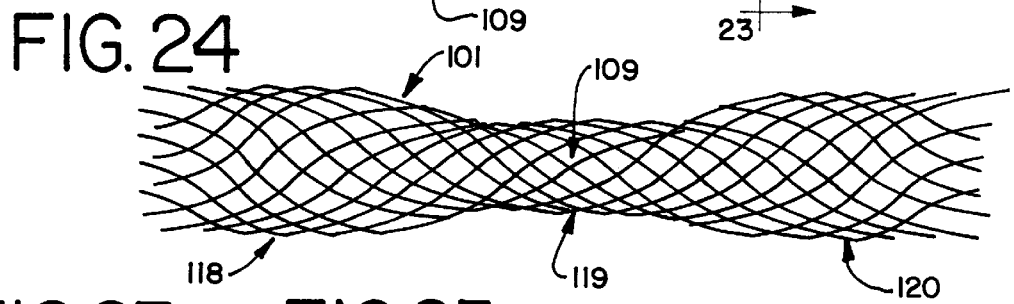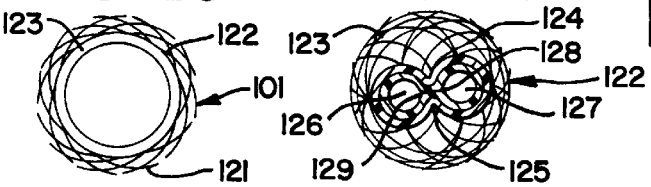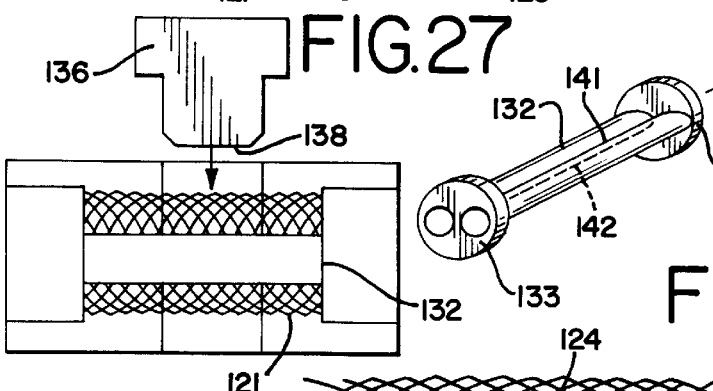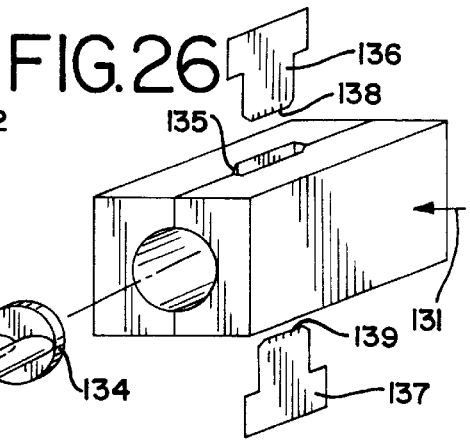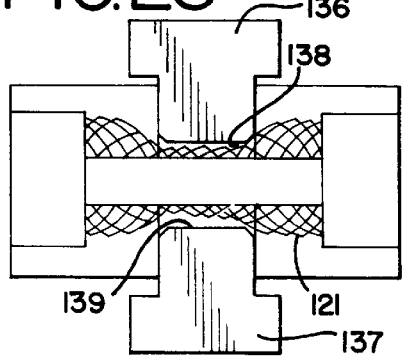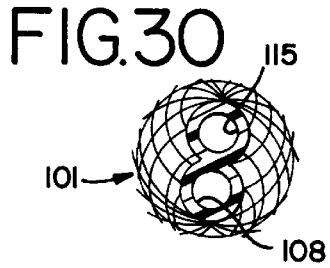

EXPANDABLE SUPPORTIVE BRANCHED ENDOLUMINAL GRAFTS

CROSS REFERENCE TO RELATED APPLICATION

This is a continuation-in-part of application Ser. No. 08/558,028, filed Nov. 13, 1995, now U.S. Pat. No. 5,632,772 and application Ser. No. 08/558,034, filed Nov. 13, 1995, now U.S. Pat. No. 5,639,278, which are each a continuation-in-part of application Ser. No. 140,245, filed Oct. 21, 1993, now abandoned.

BACKGROUND AND DESCRIPTION OF THE INVENTION

This invention generally relates to supportive endoluminal grafts which have the ability to be delivered transluminally and expanded in place to provide a graft that is endoluminally positioned and placed, with the aid of an appropriate inserter or catheter, and that remains so placed in order to both repair a vessel defect and provide lasting support at the location of the graft. In its broadest sense, the graft preferably combines into a single structure both an expandable luminal prosthesis tubular support component and a compliant graft component secured thereto. The expandable supportive endoluminal graft takes on a bifurcated or branched structure made up of components that are designed to be positioned in a bifurcated manner with respect to each other, preferably during deployment or repair and support of vessel locations at or near branching sites. Preferably, the graft component is compliant, stretchable or elastomeric and does not substantially inhibit expansion of the tubular support component while simultaneously exhibiting porosity which facilitates normal cellular growth or invasion thereinto of tissue from the body passageway after implantation.

Elastomeric vascular grafts are known to be made by various methods. Included are methods which incorporate electrostatic spinning technology such as that described by Annis et al. in "An Elastomeric Vascular Prosthesis", *Trans. Am. Soc. Artif. Intern. Organs,* Vol. XXIV, pages 209–214 (1978) and in U.S. Pat. No. 4,323,525. Other approaches include elution of particulate material from tubular sheeting, such as by incorporating salts, sugars, proteins, water-soluble hydrogels, such as polyvinyl pyrrolidone, polyvinyl alcohol, and the like, within polymers and then eluting the particulate materials by immersion in water or other solvent, thereby forming pores within the polymer. Exemplary in this regard is U.S. Pat. No. 4,459,252, incorporated by reference hereinto. Another approach involves the forming of pores in polymers by phase inversion techniques wherein a solventized polymer is immersed in another solvent and the polymer coagulates while the polymer solvent is removed. Also known are spinning techniques such as those described in U.S. Pat. No. 4,475,972. By that approach, a polymer such as a polyurethane in solution is extruded as fibers from a spinnerette onto a rotating mandrel. The spinnerette system reciprocates along a path which is generally parallel to the longitudinal axis of the mandrel and at a controlled pitch angle. The result is a non-woven structure where each fiber layer is bound to the underlying fiber layer.

Also known are stent devices, which are placed or implanted within a blood vessel or other body cavity or vessel for treating occlusions, stenoses, aneurysms, disease, damage or the like within the vessel. These stents are implanted within the vascular system or other system or body vessel to reinforce collapsing, partially occluded, weakened, diseased, damaged or abnormally dilated sections of the vessel. At times, stents are used to treat disease at or near a branch, bifurcation and/or anastomosis. This runs the risk of compromising the degree of patency of the primary vessel and/or its branches or bifurcation, which may occur as a result of several problems such as displacing diseased tissue, vessel spasm, dissection with or without intimal flaps, thrombosis and embolism.

One common procedure for implanting a stent is to first open the region of the vessel with a balloon catheter and then place the stent in a position that bridges the diseased portion of the vessel. Various constructions and designs of stents are known. U.S. Pat. No. 4,140,126 describes a technique for positioning an elongated cylindrical stent at a region of an aneurysm to avoid catastrophic failure of the blood vessel wall, the stent being a cylinder that expands to an implanted configuration after insertion with the aid of a catheter. Other such devices are illustrated in U.S. Pat. Nos. 4,787,899 and 5,104,399. U.S. Pat. Nos. 4,503,569 and 4,512,338 show spring stents which expand to an implanted configuration with a change in temperature. It is implanted in a coiled configuration and then heated in place to cause the material of the spring to expand. Spring-into-place stents are shown in U.S. Pat. No. 4,580,568. U.S. Pat. No. 4,733,665 shows a number of stent configurations for implantation with the aid of a balloon catheter. U.S. Pat. No. 5,019,090 shows a generally cylindrical stent formed from a wire that is bent into a series of tight turns and then spirally wound about a cylindrical mandrel to form the stent. When radially outwardly directed forces are applied to the stent, such as by the balloon of an angioplasty catheter, the sharp bends open up and the stent diameter enlarges. U.S. Pat. No. 4,994,071 describes a bifurcating stent having a plurality of wire loops that are interconnected by an elongated wire backbone and/or by wire connections and half hitches.

Stents themselves often do not encourage normal cellular invasion and can lead to undisciplined development of cells in the stent mesh, with rapid development of cellular hyperplasia. Grafts alone do not provide adequate support in certain instances. Copending application of Jean-Pierre Dereume, Ser. No. 08/546,524, entitled "Luminal Graft Endoprostheses and Manufacture Thereof" describes grafts that have the ability to carry out dilatation and/or support functions. An expandable tubular support component and an elastomeric graft component are combined into a single device wherein the graft material is secured to either or both of the internal and external surfaces of the expandable support component. The graft material is produced by a spinning technique such as that described in U.S. Pat. No. 4,475,972. Also, luminal endoprostheses with an expandable coating on the surface of external walls of radially expandable tubular supports are proposed in U.S. Pat. Nos. 4,739,762 and 4,776,337. In these two patents, the coating is made from thin elastic polyurethane, Teflon film or a film of an inert biocompatible material. A. Balko et al., "Transfemoral Placement of Intraluminal Polyurethane Prosthesis for Abdominal Aortic Aneurysm", *Journal of Surgical Research,* 40, 305–309, 1986, and U.S. Pat. Nos. 5,019,090 and 5,092,877 mention the possibility to coat stent materials with porous or textured surfaces for cellular ingrowth or with non-thrombogenic agents and/or drugs. The various patents and publications referred to hereinabove are incorporated hereinto by reference.

By the present invention, grafts which are expandable and supportive are provided that expand from a first diameter to a second diameter which is greater than the first. When it is at its first diameter, the expandable supportive graft is of a size and shape suitable for insertion into the desired body passageway. The material of the graft is substantially inert and preferably has a generally cylindrical cover and/or lining generally over the outside and/or inside surface of the expandable supportive component. Preferably, the cover and/or lining is especially advantageous because it is compliant or elastomeric and porous to encourage desirable growth of tissue thereinto in order to assist in non-rejecting securement into place and avoidance of stenosis development. The porous liner and/or cover material is compliant or elastomeric enough to allow for expansion by up to about 2 to 4 times or more of its unexpanded diameter. Components of the branched or bifurcated expandable supportive endoluminal graft preferably are deployable separately such that each component is properly positioned with respect to the other into the desired branched or bifurcated arrangement. One of the components has a portion which has at least one longitudinally disposed indent to generally define at least two leg portions for receiving one of the other components.

It is a general object of the present invention to provide an improved branched endoluminal graft that is expandable in place and, once expanded, is self-supporting.

Another object of this invention is to provide biocompatible grafts having a plurality of components that are separately expandable in vivo and that are supportive once so expanded.

Another object of the present invention is to provide an improved expandable reinforced graft that is delivered by way of introducers, balloon catheters or similar devices, and which facilitates good tissue ingrowth.

Another object of this invention is to provide an improved endoluminal graft which fully covers diseased or damaged areas for carrying out luminal repairs or treatments, such as repair of aneurysms.

Another object of the present invention is to provide an improved endoluminal graft wherein the endoprosthesis is substantially enclosed within biocompatible compliant material which is presented to the surrounding tissue and blood or other body fluid.

Another object of this invention is to provide an expandable, supportive graft that can be tailored to meet a variety of needs, including a single graft designed to address more than a single objective.

Another object of the present invention is to provide a self-expanding reinforced graft device that is delivered in its elongated and compressed state from within a tubular member and deployed by moving same out of the tubular member, which device is especially suitable for component deployment.

Another object of this invention is to provide a bifurcated trunk component that is deployed in a collapsed state and expanded in vivo to a branched device for use in treatment and/or repair at branched vessel locations.

A further object of the present invention is to provide a component branched endoluminal graft having a longitudinally creased trunk component and at least one cylindrical branch component, which components are expanded separately after endoluminal delivery and which form a bifurcated graft once positioned with respect to each other and expanded.

Another object of this invention is to provide an improved method of forming a branched endoluminal graft incorporating a longitudinal creasing procedure.

Another object of the present invention is to provide an improved method of assembling a branched endoluminal graft.

These and other objects, features and advantages of this invention will be clearly understood through a consideration of the following detailed description.

BRIEF DESCRIPTION OF THE DRAWINGS

The invention will be further elucidated in the following description with reference to the drawings, in which:

FIG. 7 is a perspective view, partially cut away, of a bifurcated expandable supportive endoluminal graft construction;

FIG. 8 is a cross-sectional view along the line 8—8 of FIG. 7;

FIG. 9 is a somewhat schematic view illustrating an early step in the implantation of a device such as shown in FIG. 7;

FIGS. 10, 11 and 12 are generally schematic views along the lines of FIG. 9 showing expansion of the main body and the branches of this bifurcated device;

FIG. 13 shows this bifurcated supportive graft after completion of the expansion procedure;

FIG. 22 is a top plan view of an embodiment of a branching trunk component in accordance with the invention;

FIG. 23 is a cross-sectional view along the line 23—23 of FIG. 22;

FIG. 24 is a side elevational view of the branching trunk component as illustrated in of FIGS. 22 and 23;

FIG. 25 is an end view of the structure as shown in FIG. 24;

FIG. 26 is a perspective, generally exploded view of an example of a fixture suitable for forming the longitudinal crease in this trunk component;

FIG. 27 is a longitudinal broken-away view of the fixture of FIG. 26 with a braided cylindrical tube positioned therein;

FIG. 28 is a view generally in accordance with FIG. 27, showing formation of opposing crease indents in the braided cylindrical tube during formation of this trunk component;

FIG. 29 is a top plan view showing assembly of supportive endoprosthesis leg components into a branching trunk component according to the invention;

FIG. 30 is an end view of the structure as shown in FIG. 29;

DESCRIPTION OF THE PARTICULAR EMBODIMENTS

Figure 1:
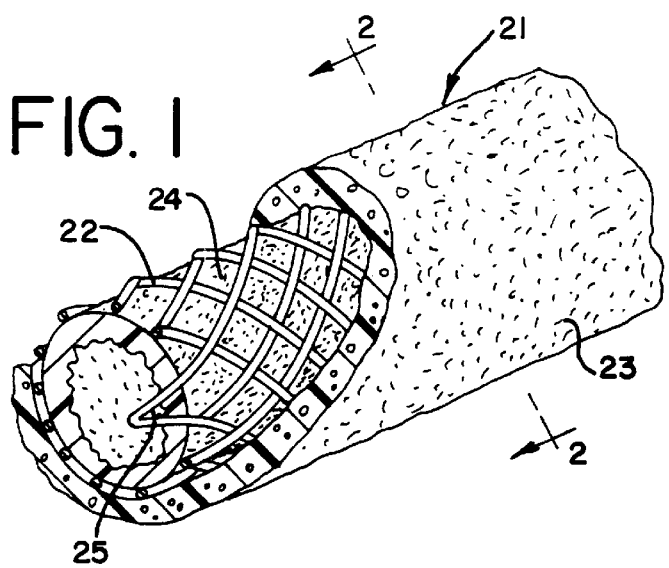
FIG. 1 is a perspective view, partially cut away, of an expandable supportive endoluminal graft construction in accordance with the invention.
Figure 2:
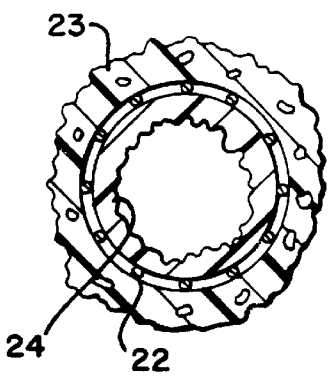
FIG. 2 is a cross-sectional view along the line 2—2 of FIG. 1.

An embodiment of expandable supportive luminal graft construction is generally illustrated in FIG. 1 at 21. This embodiment includes a braided tubular support component having generally helically wound rigid but flexible strand or wire elements, some of which have the same direction of winding but are axially displaced from one another, and others of which cross these windings and are also axially displaced with respect to each other. The actual structure can be generally braided as illustrated in Wallsten U.S. Pat. No. 4,655,771, incorporated by reference hereinto, or as found in self-expanding braided flat wire Wallstent® devices. Both a cover 23 and a liner 24 are illustrated in FIGS. 1 and 2. Either cover 23 or liner 24 can be omitted if there is no desire to substantially encapsulate the tubular support component 22.

With more particular reference to the illustrated cover 23 and liner 24, when included, they may be formed by an electrostatic spinning process in this illustrative embodiment. Details regarding electrostatic spinning techniques in general are found in Bornat U.S. Pat. No. 4,323,525 and in Bornat European patent publication No. 9,941, as well as in the Annis et al. article discussed hereinabove, the disclosures of which are incorporated by reference hereinto. With further reference to the application of this technology to the expandable supportable luminal grafts of the present invention, random pattern filaments are formed and electrostatically directed toward a charged mandrel in order to form a random pattern of electrostatically generally cross-linked filaments which take on the configuration of a mat having a cylindrical shape. The filament diameters are particularly fine, as is the pore size of the mat so constructed. A typical range of filament diameters is between about 0.5 micron and about 5 microns, and a typical pore size of the electrostatically spun fiber is between about 3 microns and about 20 microns.

Figure 18:
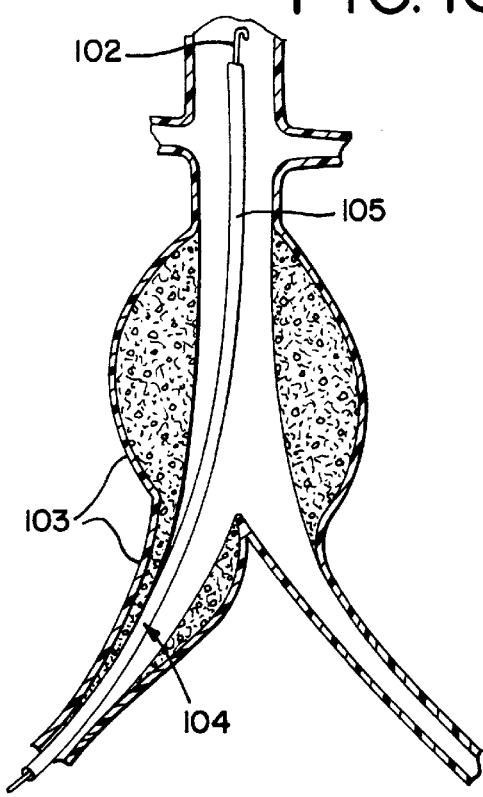
FIGS. 18, 19, 20 and 21 illustrate a component branched graft and various stages of its separate, component deployment within a body vessel to repair an aneurysm, FIGS. 18 and 19 showing deployment of a preferred branched, longitudinally indented trunk component, and FIGS. 20 and 21 showing separate deployment of two branch components within the trunk component.
Figure 19:
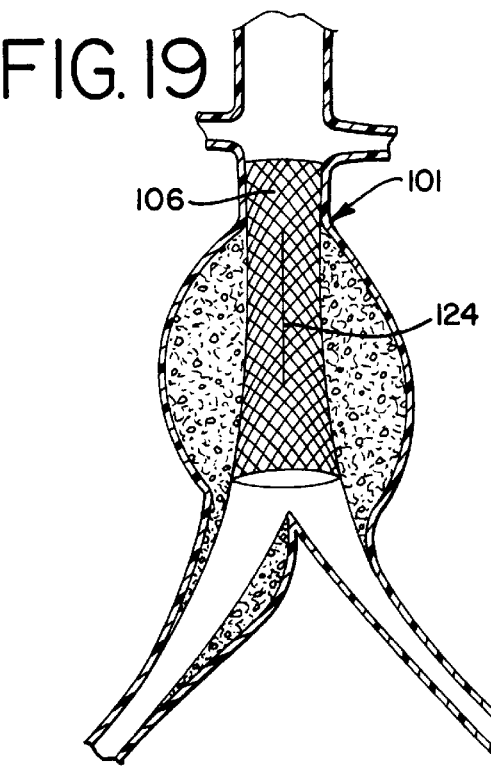
Figure 20:
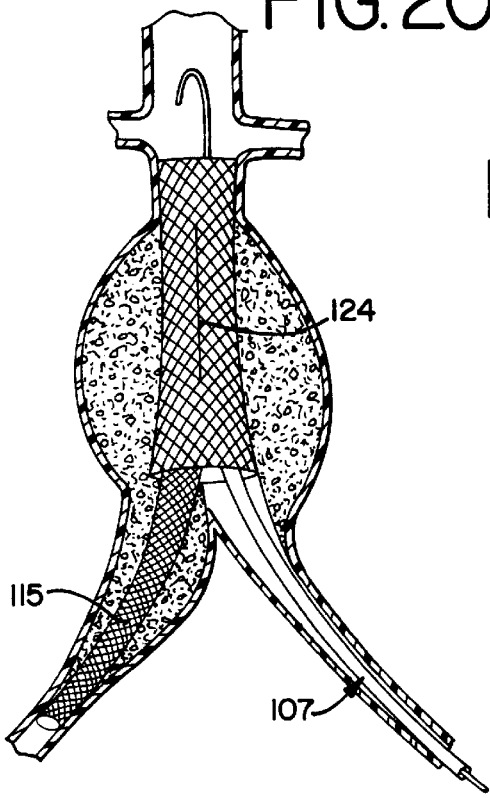

Liner 24 is formed directly on the rotating mandrel by this electrostatic spinning procedure. Thereafter, one of the tubular support components discussed herein, such as the generally braided tubular support 22, is placed over the liner 24 still on the mandrel. In the case of the tubular support 22 in a form that is not spring loaded, this includes longitudinally extending the tubular support 22, such as by pulling one or both of its ends, which thereby decreases its diameter so that it fits snugly over the liner 24. When the generally braided tubular support 22 is of a spring-into-place type, a hold-down member (such as shown in FIGS. 18 and 20) is used to prevent automatic radial expansion prior to deployment. When the expandable supportive graft 21 is to include a cover 23, the mandrel is again rotated, and the electrostatic spinning is again accomplished in order to form the cover 23 directly over the tubular support 22. This will also create some bonding between the thus formed cover 23 and the liner 24 at openings between the strands or wires of the woven tubular support 22 or the like. This bonding can be facilitated by uniformly compressing the outer fibers with a soft silicone roller or sponge such that the still tacky outer fibers bond to the inner fibers thereby encapsulating the tubular support within the graft.

Bonding may also be achieved in this or other embodiments by heat welding and/or by the use of adhesives such as hot melt adhesives, primers, coupling agents, silicone adhesives, and the like, and combinations of these. Examples include aliphatic polycarbonate urethane hot melts and silicone rubber adhesives.

It is important to note that each of the cover 23 and the liner 24, when either or both are present, is made of an elastomeric material which retains its compliant properties after construction of the expandable supportive graft 21 is completed. In this regard, the graft itself is also elastomeric and compliant. Accordingly, the graft 21 is delivered transluminally, such as by being pulled down onto the balloon of a catheter or into an inserter tube and then percutaneously inserted and positioned to the location where the repair is needed. For a non-spring loaded graft, the balloon is then inflated to longitudinally shorten and radially expand the graft 21 into engagement with the vessel walls. Because of the compliance of the cover 23 and/or liner 24, and because of the hoop strength of the braided tubular support 22, the graft 21 will remain in place. In the illustrated embodiment, ends 25 of the tubular support are exposed and are not covered by the cover 23. This allows the exposed end portions 25 to directly engage the vessel wall, if desired in the particular application, in order to assist in anchoring the graft 21 in place. Liner 24 also can be sized so as to not cover the exposed ends 25, or it can extend to or beyond the edge of the ends 25 when it is desired to avoid or minimize contact between the tubular support and the blood or other fluid flowing through the vessel being repaired or treated.

Alternatively, when a braided tubular support such as that illustrated in FIGS. 1 and 2 is incorporated into the graft according to the present invention in a non-spring-loaded form, transluminal delivery can be made by way of a catheter or tool having means for longitudinally compressing the endoprosthesis until it has expanded radially to the desired implanted diameter. Such equipment typically includes a member that engages one end of the endoprosthesis and another member which engages the other end of the endoprosthesis. Manipulation of proximally located controls then effects relative movement of the members toward each other in order to thereby longitudinally compress the endoprosthesis. Delivery tools for spring-loaded grafts include a sleeve that maintains the graft at its compressed diameter until the graft is positioned for deployment such as from the end of an insertion catheter to its auto-expanded state.

Figure 3:
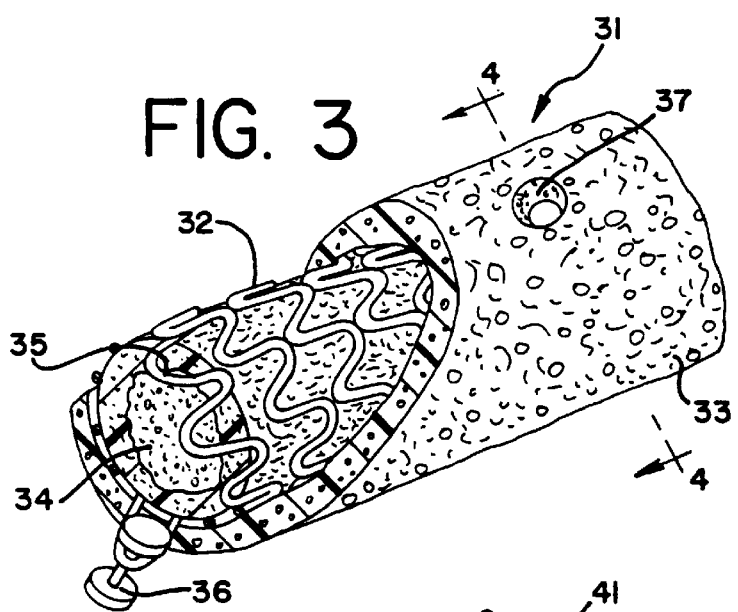
FIG. 3 is a perspective view, partially cut away, of another embodiment of the expandable supportive endoluminal graft construction.
Figure 4:
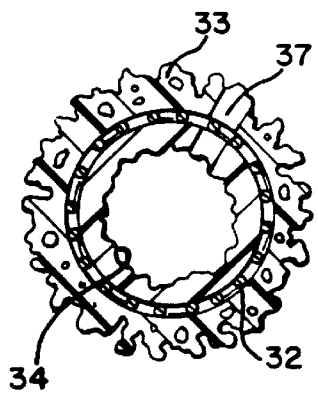
FIG. 4 is a cross-sectional view along the line 4—4 of FIG. 3.

With reference to the embodiment illustrated in FIGS. 3 and 4, an expandable supportive graft is illustrated at 31. The illustrated tubular support component 32 is constructed of sinusoidally configured wire helically wound into a tubular shape. General structures of these types are generally discussed in Pinchuk U.S. Pat. No. 5,019,090, incorporated by reference hereinto. A cover 33 can be positioned over the tubular support 32 and/or a liner 34 can be positioned along its lumen. In this illustrated embodiment, the cover 33 and liner 34 are constructed of porous polymers, the pores thereof having been made by elution or extraction of salts and the like, such as described in MacGregor U.S. Pat. No. 4,459,252, incorporated by reference hereinto. Generally speaking, the porosity is determined by the size of the elutable particles as discussed herein and by the concentration of those particles as a percent by volume of a pre-elution mixture thereof with the polymer of the cover or liner. When a graft 31 having both a cover 33 and a liner 34 is prepared, a mandrel or rod is dipped into a liquid polymer having elutable particles as discussed herein dispersed therewithin. After dipping, the polymer covered rod is contacted with, such as by dipping or spraying, a solvent, for the elutable particles, such as water, thereby forming the eluted porous liner 34. Thereafter, the tubular support 32 is positioned thereover and pressed down into the liner. Then, the rod and the assembly thereon are again dipped into the mixture of polymer and elutable particles, followed by setting and contact with solvent to remove the elutable particles in order to form the eluted porous cover 33. It is also possible to directly extrude the particle-containing polymer into a tubular shape.

Elutable particles which can be used in the making of the eluted porous cover 33 and liner 34 include salts such as sodium chloride crystals, sodium carbonate, calcium fluoride, magnesium sulfate and other water-soluble materials that are readily dissolved by the utilization of water as an elution medium. Other particles that are soluble in organic solvents and the like can be substituted as desired. Further particles include sugars, proteins, and water-soluble hydrogels such as polyvinyl pyrrolidone and polyvinyl alcohol. Suitable polymer materials are as discussed elsewhere herein, the pore size being on the order of about 10 microns to about 80 microns.

As with the other embodiments, when desired, ends 35 of the support component 32 can be exposed either on one or both of its cylindrical faces in accordance with the needs of the particular repair or treatment to be carried out. With this approach, the exposed ends 35 will assist in maintaining the graft 32 in place by mechanical engagement between the exposed ends 35 and the vessel being repaired or treated and/or by tissue ingrowth. The anchoring aspect of the exposed ends of the tubular support can be enhanced by continued radial expansion of the balloon or other deployment means which will permit the exposed ends to expand radially outwardly in an amount somewhat greater than that of the rest of the expandable supportive graft and into the surrounding tissue. It is also contemplated that mechanical means can be used to assist in joining the exposed ends of this embodiment or of other embodiments to the vessel wall. An illustrative example in this regard is the use of transluminally delivered staples which can take on the appearance of rivets. Especially advantageous are staples made of an elastomeric material. Illustrated staples are shown at 36 in FIG. 3. They can be incorporated at other locations as well along the graft. One or more windows 37 can be formed through the cover and/or liner and/or tubular support in order to feed outside branch arteries or other vessels.

Figure 5:
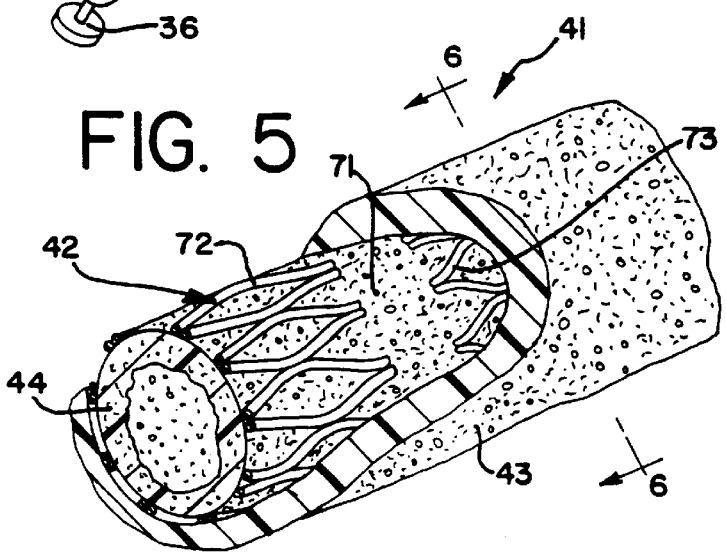
FIG. 5 is a perspective view, partially cut away, of a further embodiment of the expandable luminal graft construction.
Figure 6:
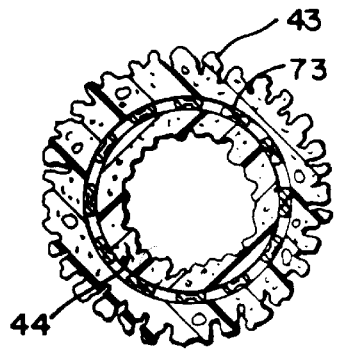
FIG. 6 is a cross-sectional view along the line 6—6 of FIG. 5.

FIGS. 5 and 6 illustrate a further embodiment of an expandable supported graft, generally designated as 41. Shown is a mesh tubular support component, generally designated as 42, such as those of the type illustrated in Palmaz U.S. Pat. No. 4,733,665, incorporated by reference hereinto. These are non-woven mesh-type cylinders or slotted tubes wherein most or all of the individual components are either integrally joined together such as by welding or are integrally formed from a single tube. The resulting endoprostheses are malleable enough so as to be expandable by a balloon of a catheter. Usually, these endoprostheses have particularly high hoop strengths.

Cover 43 and/or liner 44 are made of polymers rendered porous by phase inversion techniques. In accordance with these techniques, a polymer such as a polyurethane is dissolved in a solvent therefor, for example a water-soluble polar solvent, such as dimethyl acetamide, tetrahydrofuran and the like, in order to form what is known as a lacquer. A mandrel or rod is dipped into the lacquer. Thereafter, the dipped rod is contacted with an inversion solvent, such as by dipping in water or a mixture of alcohol and water. This inversion solvent must readily dissolve the polymer solvent of the lacquer, while at the same time being a poor solvent for the polymer. Under these conditions, the polymer coagulates and the polymer solvent of the lacquer is removed and replaced with the inversion solvent. The inversion solvent pulls the polymer solvent out of the polymer on the rod and forms particularly fine pores having a pore size on the order of about 0.5 micron to about 20 microns. The thus formed liner 44 having phase inversion pores is then dried.

Next, the tubular support component 42 is secured over the liner 44 and is preferably radially compressed onto and into the liner. Thereafter, the cover 43 having phase inversion pores is formed in accordance with the same phase inversion steps as discussed hereinabove for preparation of the liner 44. If desired, either the liner or the cover can be omitted. Cover 43 and liner 44 are thus formed in accordance with a displacing step wherein precipitating non-solvent molecules are substituted for non-precipitating solvent molecules dispersed throughout the lacquer coating. This procedure develops advantageous elastic characteristics. Further details regarding the phase inversion procedure are found in Lymann et al. U.S. Pat. No. 4,173,689, incorporated by reference hereinto.

FIGS. 7 and 8 illustrate an embodiment wherein the graft takes the form of a bifurcated expandable supportive graft, generally designated at 51. Included is a joined-ring bifurcated tubular support 52. Also shown are a bifurcated cover 53, a bifurcated lining 54 and exposed ends 55, 56, 57. This particular bifurcating graft is well-suited for insertion into a branching vessel.

The tubular support includes a plurality of rings or loops 58 connected by flexible interconnections 59. Constructional details of embodiments of the rings or loops 58 and of the flexible interconnections 59 are found in MacGregor U.S. Pat. No. 4,994,071, incorporated by reference hereinto. The flexible interconnections 59 join the rings or loops 58 into a configuration having a main body or trunk 61 and one or more branches 62. Flexible interconnections 59 extend longitudinally from the axis of each of the main body or trunk 61 and branch 62, 63. At least one such flexible interconnection joins each branch to the trunk. The loops 58 in the main body are substantially parallel to each other, and the loops 58 in each branch 62, 63 are substantially parallel to each other.

The bifurcated cover 53 and bifurcated liner 54 must each, when provided, be especially elastomeric so as to follow the expansion and contraction of the rings or loops 58 that takes place during preparation, transluminal insertion, deployment and the like. Cover 53 and liner 54 will also take on a bifurcated construction. In one embodiment, the liner and/or cover for each of the trunk 61 and branch 62, 63 are made on a cylindrical mandrel, assembled and joined, such as by suitable biocompatible adhesive, fusion, sewing, suturing or other means of joining and/or sealing. Alternatively, a Y-shaped or branched mandrel can be used. The bifurcating liner is then formed thereon by processes such as those discussed herein, including electrostatic spinning, or dipping followed by elution or phase inversion procedures much in the same manner as described herein when straight cylindrical mandrels or rods are used for constructing the non-bifurcated grafts in accordance with this invention. Fiber winding can also be practiced. Bifurcated cover 53 is made in a similar manner by application of the porous cover material over the bifurcated endoprosthesis.

With reference to the bifurcated endoprosthesis, the bifurcated cover 53 and/or bifurcated liner 54 could be made by fiber winding approaches, such as those described in Wong U.S. Pat. No. 4,475,972, the subject matter thereof being incorporated by reference hereinto. Polymer in solution is extruded into fibers from a spinnerette onto a rotating mandrel. The spinnerette is reciprocated along the longitudinal axis of the mandrel at a controlled pitch angle, resulting in a non-woven cylinder wherein each fiber layer is bound to the underlying layer. Control of the pitch angle allows for control of the compliance and kink resistance of the cover and/or liner. In an especially advantageous arrangement when using these fiber spinning techniques in forming an expandable supportive graft in accordance with the general aspects of this invention which has both a liner and a cover, the cover is physically bonded to the liner by the use of an electrostatic field to enable penetration of the cover overlay of fibers through the interstices of the support components in order to improve the bonding of the cover and/or liner fibers to each other and/or to surfaces of the support component.

With more particular reference to balloon deployment of expandable supportive grafts, this is illustrated with some particularity in connection with bifurcated endoluminal grafts in FIGS. 9, 10, 11, 12 and 13. As shown in FIG. 9, two guidewires 64, 65 are inserted into the bifurcating vessel, each of them into different legs 66, 67 of the bifurcating vessel. Thereafter, the unexpanded bifurcated expandable supportive graft 51 is slipped over the proximal ends of the guidewires and routed to the branches of the blood vessel. The unexpanded bifurcated graft can be introduced from an arteriotomy proximal to the bifurcation such as from the brachial artery in the arm, or the unexpanded bifurcated graft can be introduced from the femoral artery in the leg, pushed proximally past the bifurcation and then pulled back distally into both iliacs to form the trunk and bifurcation.

The two branches 62, 63 of the graft 51 are routed separately over the guidewires 64, 65, respectively, and guided, typically with the help of a guide catheter, into the patient until the graft is positioned as shown in FIG. 9. The graft 51 is initially fixed in place as follows. One of the guidewires 65 is removed, and a balloon catheter 68 is inserted into the main body or trunk 61 and inflated to expand the trunk 61 into contact with the vessel walls. This deployment is suitable to secure the graft 51 in place at that location of the vessel.

The balloon of balloon catheter 68 is then deflated. If this balloon catheter is also suitable for use in expanding the branches 62, 63 of the graft 51, same is then inserted into an unexpanded branch 62 and radially expanded as generally shown in FIG. 11. If the balloon of catheter 68 is not suitable in this regard, then another balloon catheter 69 effects this function. FIG. 12 shows inflation of the other branch 63 of the graft 51 in a similar manner. FIG. 13 illustrates the fully deployed and expanded bifurcated support graft 51 positioned in place within the bifurcated location. Alternatively, a bifurcated dilation balloon on a bifurcated catheter (not shown) can replace the single-balloon catheter(s) 68, 69.

Preferably the branched and assembled expandable supportive graft is of the spring-into-place type; as such, it will be manipulated to be reduced in diameter and placed within an overlying and bifurcated restraining guiding catheter or the like and will be passed over guidewires and contained within the guiding catheter until proper placement within the bifurcating location. This type of bifurcated expandable supportive graft is deployed by being ejected into place, typically by advancing a small inner catheter through the guiding catheter into contact with the bifurcating graft in accordance with the procedure generally used for spring-into-place stents.

The deployment procedures illustrated in FIGS. 9 through 13 can be characterized as prograde deployment. Retrograde deployment is also possible. The entire bifurcating graft for retrograde deployment is advanced over a single guidewire through one branch of the blood vessel past the point of bifurcation. A second guidewire is then steered down the opposite limb of the graft, and a snare is used. The snare, which is passed retrograde through the opposite vessel, is then used to pull the guidewire into place. Partial balloon inflation in the unbranched or trunk portion of the blood vessel is then used to draw the graft down into position prior to balloon dilatation of both the trunk and branched portions of the graft. Because blood flow is prograde under these circumstances, the contact between the bifurcation of the graft and the bifurcation of the blood vessel helps to prevent the graft from migrating distally, thus reducing the need for active fixation of the graft to the blood vessel.

Figure 14:
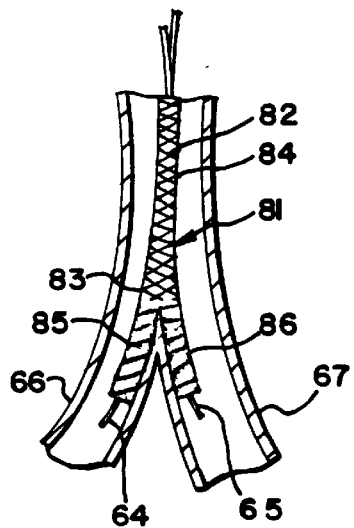
FIG. 14 illustrates another embodiment of a bifurcated expandable supportive endoluminal graft construction.

Another bifurcated endoprosthesis or expandable supportive graft is generally designated 81 in FIG. 14. Separate components are included. In this case tubular supporting component(s) are, prior to deployment, separate from a trunk component. In this embodiment, a fully independent tubular supporting component 82 is located at the trunk position of the graft 81. A bifurcated stretchable wall 83 is in contact with the independent tubular supporting component 82 as either or both of a cover or liner. In addition to being substantially coextensive with the independent tubular supporting component 82 at a trunk portion 84 thereof, the stretchable wall 83 includes at least two generally tubular stretchable branch sleeves 85, 86 which are initially devoid of a supporting component. Separate tubular supporting components 87, 88 (FIGS. 16 and 17) are also included.

Figure 15:
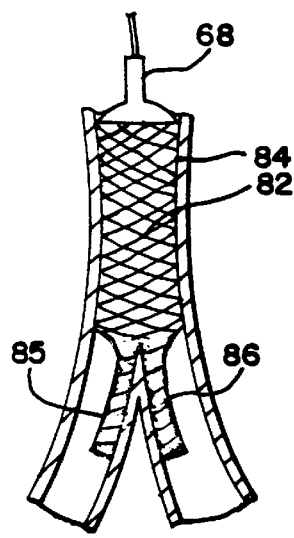
FIGS. 15, 16 and 17 illustrate implantation and assembly of the graft of FIG. 14.

Implantation of this bifurcated expandable supportive graft is depicted in FIGS. 14, 15, 16 and 17. Dual guidewires 64, 65 can be used to properly position the unexpanded bifurcated graft 81 within the bifurcating vessel as shown in FIG. 14. A balloon catheter 68 or similarly functioning device is inserted into the main body of the device so as to expand the independent tubular supporting component 82 and the trunk portion 84 of the bifurcated stretchable wall 83. This deployment initially secures the bifurcated supporting graft into place at that location of the vessel, as shown in FIG. 15. The balloon catheter is then deflated and removed or positioned for use in the next step.

Figure 16:
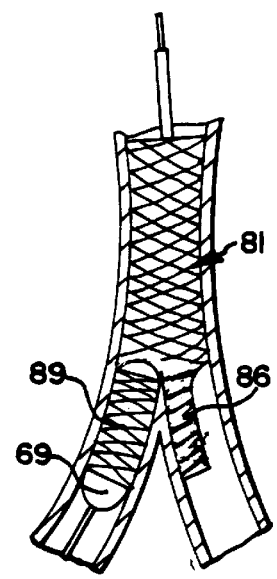
Figure 17:
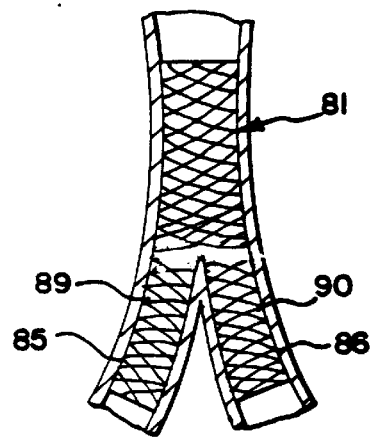

A suitable balloon catheter 69 or the like is next used to deploy and expand in place a branch tubular expandable supporting component 89, as illustrated in FIG. 16. A similar step deploys and expands in place another branch tubular expandable supporting component 90, as generally shown in FIG. 17. The bifurcated stretchable wall 83 and the expandable supporting components may be made with the materials and constructions discussed herein and may be subjected to various treatments as discussed.

A further bifurcated endoprosthesis or expandable supportive graft is one in which the separate components are each expandable supportive graft members. These separate components are illustrated in FIG. 18 through FIG. 21, which also illustrate their separate deployment with respect to each other within an aortic trunk. Same is shown in connection with treating an aneurysm such as an abdominal aorto-iliac aneurysm. The device includes a trunk component 101 which, in the illustrated use, is designed to extend from below the renal arteries to a location between the proximal neck of the aneurysm and the aorto-iliac bifurcation. It will be understood that this trunk component could also be shorter so that it terminates just below the proximal neck of the aneurysm, for example of a length which terminates within the dent or crease 124. In addition, the component bifurcated expandable supportive graft of this embodiment is self-expanding and is deployed by means an introducer containing compressed expandable supportive graft components.

More particularly, and with reference firstly to FIG. 18, a guidewire 102 is first inserted in accordance with known procedures so as to traverse the aneurysm 103. Next, an introducer, generally designed as 104 having the trunk component therewithin in a radially compressed state is inserted over the guidewire 102. The introducer is maneuvered such that it is properly positioned as desired, in this case at a location distal of the distal end of the aneurysm. Then, the sheath 105 of the introducer is withdrawn, such as by sliding it in a proximal direction while the remainder of the introducer 104 remains in place. As the sheath is withdrawn, the trunk 101 expands, eventually achieving the deployed or implanted position shown in FIG. 19. At this stage, the distal portion 106 of the trunk is well anchored into the blood vessel wall and is suitably deployed.

Figure 21:
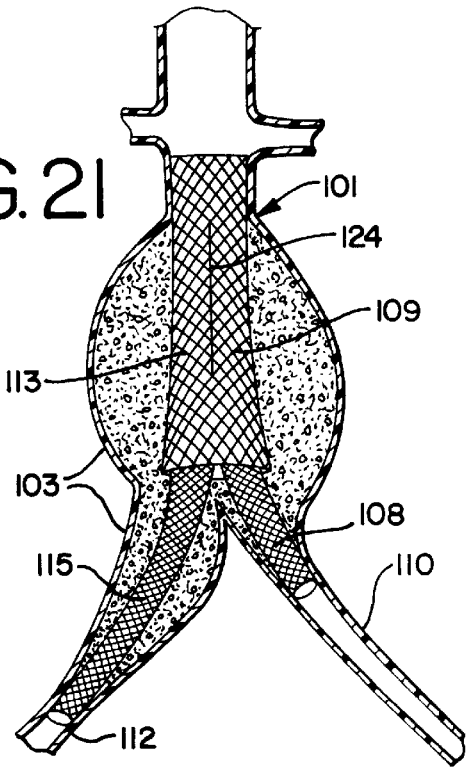

FIG. 20 shows an introducer, generally designated as 107, having an independent tubular expandable supportive graft leg component 108 (FIG. 21) radially compressed therewithin. In this illustrated embodiment, this leg component is an iliac component of the bifurcated supportive graft being assembled within the body vessel. The introducer 107 is advanced until this iliac component is moved into a leg 109 of the already deployed trunk component 101. This positioning is illustrated in FIG. 21. It will be noted that the iliac tubular supportive graft component 108 extends from well within the leg 109 to a location proximal of the aneurysm in the iliac artery 110.

In a previous step, a guidewire had been passed through the appropriate vessel to iliac artery 112 until it crossed the aneurysm 103, while passing through the other leg 113 of the deployed trunk component 101. When the introducer for the previously radially compressed iliac component 115 had been removed, the component 115 had expanded radially and was deployed. Thus, the entirety of the bifurcated endoprosthesis or expandable supportive graft in accordance with this embodiment is fully deployed and assembled together as shown in FIG. 21, as well as generally depicted in FIGS. 29 and 30.

It will be noted that it is not required to actually attach the trunk component 101 and the tubular components 108, 115 together. In other words, these components are generally telescopically positioned with respect to each other. This telescopic feature allows some slippage between the trunk component and the tubular leg components, thereby providing a telescopic joint which functions as a slip bearing. It will be appreciated that it is generally desirable to firmly anchor portions of the bifurcated endoprosthesis within healthy vessel wall tissue. This can be achieved by the hoop strength of the supportive graft or by taking measures to enhance hoop strength at its ends, or by providing grasping structures such as hooks, barbs, flared ends and the like.

During pulsetile blood flow and possibly during exercise by the person within which the endoprosthesis is implanted, tension and elongation forces are imparted to the endoprosthesis. In structures that do not have a telescopic joint or some other means to relieve the stress developed by this tension, a considerable amount of stress can be placed on the anchoring sites and/or the attachment components, potentially allowing for dislodgement at the anchoring sites or breakage of attachment components.

FIGS. 22, 23, 24 and 25 further illustrate a trunk component 101. It includes a common trunk portion 118 and a branched portion, generally designated as 119. The branched portion includes the legs 109 and 113. In this embodiment, a further common trunk portion 120 is located opposite the other common trunk portion 118 and extending from the branched portion 119. Thus, the overall configuration of the trunk component is that of a double-lumen length located between two single-lumen lengths. The common trunk portion 118 can be positioned, for example, in the aortic artery, the branched portion 119 provides a bifurcation structure to direct blood flow into the two iliac arteries, and the further common trunk portion 120 facilitates deployment of the leg components into the branched portion 119, acting in the nature of a funnel for each guidewire, introducer and contracted leg component.

Trunk component 101 includes a stent or tubular supporting component 121. Also included is a liner, generally designated as 122. A further liner 123 preferably is located interiorly of the liner 122. Liners 122, 123 are secured within the stent component 121 in order to provide proper porosity for an endoprosthesis.

Trunk component 101 includes one or more indents, such as indent 124 and indent 125. A third, a fourth, or further indents can be provided depending upon the degree of branching desired. It will be appreciated that one or more tubular expandable supportive leg graft components will be provided in order to slide into the branched passageways which are thus defined by the indent(s). In the illustrated embodiment, one such leg component 108 slidingly engages an opening 126 of the trunk component leg 109, while a second leg component 115 slidingly and expansively fits within opening 127 of the leg component 115.

Figure 31:
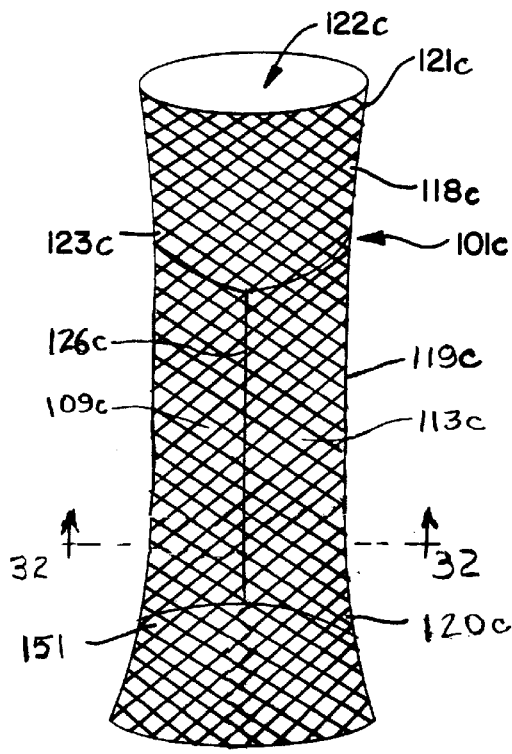
FIG. 31 is a perspective view of another embodiment of a branching trunk component in accordance with the invention.
Figure 32:
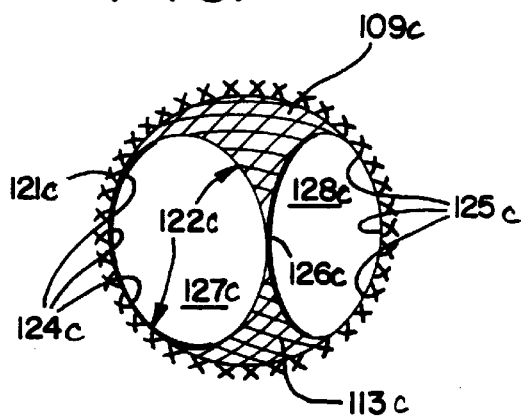
FIG. 32 is a cross-sectional view along the line 32—32 of FIG. 31.
Figure 33:
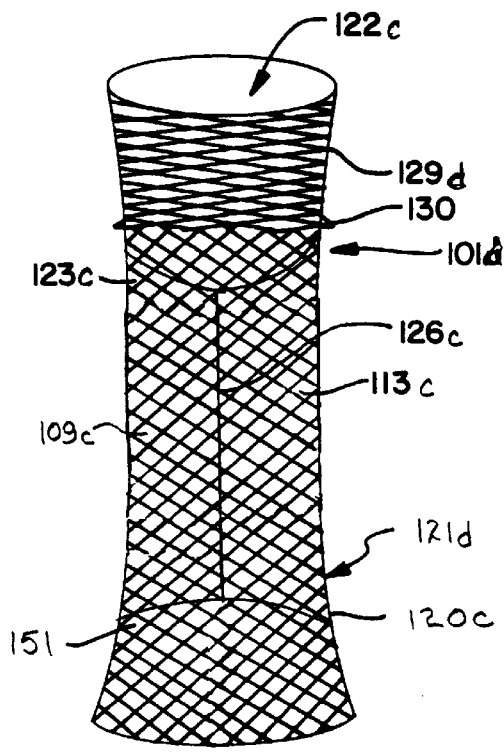
FIG. 33 is a perspective view of a modified embodiment of a branching trunk component, having a section of enhanced hoop strength.

With particular reference to FIGS. 31–33, this shows a trunk component 101c which has a function and a configuration along the lines of trunk component 101, except only the liner defines the indent or indents. In this arrangement, the tubular supporting component is cylindrical in cross-section substantially throughout its length.

FIG. 31 illustrates the trunk component 101c. It includes a common trunk portion 118c and a branched portion, generally designated as 119c. The bifurcated or branched portion includes the legs 109c and 113c. In this embodiment, a further common trunk portion 120c is located opposite the other common trunk portion 118c and extends from the branched or bifurcated portion 119c. Thus, as with trunk component 101, the overall configuration of trunk component 101c is that of a double-lumen length located between two single-lumen lengths.

Trunk component 101c includes a stent or tubular supporting component 121c, as perhaps best seen in FIG. 32. Also included is a liner, generally designated as 122c. This liner 122c has a body portion 123c and the legs 109c and 113c which open into another body portion 151.

Each leg 109c, 113c is secured to the generally tubular stent component 121c at outside portions thereof, particularly at adhesion zones 124c and 125c. The remainder of the leg portions 109c and 113c are not so bonded to the stent portion 121c. This facilitates formation of the leg portions, which are typically pinched along the length of the legs in order to form at least one internal seam 126c. Leg openings 127c and 128c are thereby generally defined between this seam 126c and the adhesion zones 124c and 125c.

In FIG. 33, means are included in the trunk component 101d which provides enhanced securement upon implantation. A stent component 129d is included which has a substantially higher pitch angle (for example, between about 140° and 180°) than does the stent portion 121d therebelow within which the legs are positioned (for example, at a pitch angle of between about 70° and 90°). This higher pitch angle zone imparts a greater hoop strength upon deployment than does the stent 121c of the trunk component 101c. A barb 130 is also shown in order to further assist in securement of the endoprosthesis to the artery wall. When desired, the barb-type of structure can be a backing ring and barb formed out of the stent strand during its formation into the cylindrical supportive member.

Any of the various expandable supportive endoluminal graft, or stent graft, constructions discussed or referred to herein can be used in order to construct devices in accordance with this embodiment. Other modifications may also be incorporated, including tubes having stepped diameters or conical ends. The stent component can be made with flat wires or with pairs of wires or multifilament wires. They can incorporate balloon expandable stents, self-expanding stents, and combinations of balloon expandable stents and self-expanding stents. Use can be made of ancillary equipment such as endoluminal stapling devices or suturing devices in order to facilitate securement at the aneurysm neck, for example. Also, a portion of the stent component without a liner component or the like thereon can project at the proximal end of the endoluminal component, such as at a location which would be above the renal arteries. The objective is also to help to secure the device in place.

The prosthesis as discussed is deployed to replace or repair tubular bodies such as blood vessels, tracheas, ureters and the like, accommodating more than one conduit in order to divert flow to other branches of the tubular body. This allows for repair of a bifurcated area which is difficult to repair using a single-lumen device or a plurality of individual single-lumen devices. It is suitable for repair of damages branched conduits or, conversely, to repair conduits which converge into a single branch.

A preferred use for the bifurcating endoluminal grafts discussed herein is for insertion into a branching blood vessel. Same is typically suitable for use in the coronary vasculature (the right, left common, left anterior descending, and circumflex coronary arteries and their branches) and the peripheral vasculature (branches of the carotid, aorta, femoral, popliteal arteries and the like). These bifurcated devices are also suitable for implantation into other branching vessels such as in the gastrointestinal system, the tracheobronchial tree, the biliary system, and the genitourinary system.

It will be appreciated that the expandable supportive grafts in accordance with the present invention will dilate and/or support blood vessel lesions and other defects or diseased areas, including at or in proximity to sites of vascular bifurcations, branches and/or anastomoses. The expandable supportive graft is an integral structure that incorporates the expandable support component into the wall or walls of the elastomeric graft. Covers and/or linings that make up the grafts interface with body components that facilitate normal cellular invasion without stenosis or recurrent stenosis when the graft is in its expanded, supportive orientation. The graft material is inert and biocompatible. The expandable supportive graft can be expanded from a smaller diameter insertion configuration to a larger diameter implantation configuration by the application of radially outwardly directed forces provided by expanding the endoprosthesis with a balloon catheter, using an ejection tube that allows a spring-into-place structure to be deployed from the end of a catheter into its expanded configuration, or by using a support component made of certain alloys exhibiting thermotransition characteristics by which they expand when heated, for example.

In addition to the support component structures illustrated herein, support structures include others having spring characteristics and those having a coil with circumferentially oriented fingers such as shown in Gianturco U.S. Pat. No. 4,800,882, incorporated by reference hereinto. U.S. Pat. Nos. 5,061,275, 5,219,355 and 5,336,500 relate to expanding or self-expanding endoluminal devices. Typically, these devices center on the use of a metallic structure imparting expansion attributes. U.S. Pat. Nos. 4,994,071 and 5,360, 443 describe bifurcated devices which use expandable metallic stent structures and textile materials allowing branching of fluid flow. In general, materials of these patents, incorporated by reference hereinto, can be utilized in constructing components of the present invention.

More specifically, the tubular supportive component preferably is a braided tubular stent body made of metal alloy or any other material that is flexible, while being rigid and resilient when thus braided. Spring-type metals are typically preferred, such as stainless steel, titanium, stainless steel alloys, cobalt-chromium alloys, including alloys such as Elgiloy, Phynox and Conichrome. Thermal transition or memory function alloys such as nickel-titanium alloys including Nitinol are also suitable. Malleable metals including tantalum would be especially suitable for a structure that is not self-expanding.

Concerning the materials for the liner(s), they are typically polymeric materials in the form of a membrane or textile-like material, the objective being to reduce the porosity of the stent for proper tissue ingrowth and fluid tightness. Exemplary polymeric materials include polyesters such as polyethylene terephthalate, polyolefins such as polypropylene, or elastomeric materials such as polyurethane or silicone rubber. Combinations of these materials are also possible. In an especially preferred arrangement, the exterior liner which engages the tubular supportive component 121, when provided, is made of a double tricot polyester mesh knit, typically a Dacron type of material, while the interior liner, 122c is made of a polyurethane. In an especially preferred arrangement, a thin coating or cover of polymer is provided over the braided wires of the tubular supportive component.

With further reference to the material out of which the cover and/or liner of the grafts in accordance with the present invention are made, the material must be stretchable with respect to the support component so that it will follow the movement of the endoprosthesis between its fully collapsed and expanded or implanted configurations. Polyurethanes are preferred. Particularly preferred is an especially crack-resistant, elastomeric and pliable polycarbonate urethane as described in Pinchuk U.S. Pat. Nos. 5,133,742 and 5,229,431, incorporated by reference hereinto.

In addition, various surface treatments can be applied to render the surfaces of the expandable supported graft more biocompatible. Included are the use of pyrolytic carbon, hydrogels and the like. The surface treatments can also provide for the elution or immobilization of drugs such as heparin, antiplatelet agents, antiplatelet-derived growth factors, antibiotics, steroids, and the like. Additionally, the coating and/or liner can be loaded with drugs such as those discussed herein, as well as lytic agents in order to provide local drug therapy.

It will be noted that the indent(s) such as indents 124, 125 and the seams(s) such as internal seam 126c are longitudinally disposed and generally define at least two leg portions, each with a diameter less than the diameter of the main body. Each indent has an internal longitudinal surface such as longitudinal edge 128, 129. These edges can be in contact with one another. If desired, they can be secured together such as with sutures, adhesives, wires, clips or the like (not shown). One or two such indents or creases produce an asymmetrical or a symmetrical bifurcation as desired. In another exemplary approach, three indents would form a trifurcated device. Additional creases can be provided insofar as is allowable by the braided wire mesh density and diameter.

Seam 126c can be formed by joining together two or more longitudinal portions of the liner 122c. When two such longitudinal portions are joined together, they are generally opposite to each other. When three such longitudinal portions are joined together, they are approximately 120° from each other along the circumference of the liner 122c, and three legs are formed. When four such longitudinal portions are joined together, for example, they are spaced approximately 90° apart.

Whatever the number of indents or seams, the deformation of the braided tubular body reduces the cross-sectional area from that of the main trunk body to that of each branched area. The total cross-sectional area of the branching tubular bodies should be equal to or greater than 40% of the cross-sectional area of the main trunk body. Preferably, this area should be greater than about 70% in order to prevent any significant pressure differences along the device once deployed and implanted. For example, in a typical human, the cross-sectional area of the abdominal aorta is reduced by only about 20% when opening into the common iliac arteries.

FIG. 26 illustrates a fixture suitable for use in forming the indent or indents as permanent deformations of the braided mesh cylinder which is the tubular supportive component for this embodiment. Fixture 131 in the configuration as illustrated is used for shaping a symmetrical bifurcated design. The braided cylinder is longitudinally compressed and placed over the mandrel 132, this placement being generally shown in FIG. 27. End caps 133, 134 lock the tubular supportive component 121 in its compressed state. Same is then placed into the fixture 131, as generally shown in FIG. 26. Slits 135 are positioned parallel to the longitudinal axis and on opposite sides. This permits the slipping of blades 136, 137 into the fixture 131 and thus into engagement with the tubular supportive component. Edges 138, 139 of the blades then engage and crease the tubular supportive component 121 between the blade edges 138, 139 and the troughs 141, 142 of the mandrel 132.

It will be appreciated that the length of the blade edges 138, 139 can be varied in order to create a desired length of deformation on the main body of the trunk component. In addition, branching areas thus formed can be made of different sizes by varying the size of the individual cylindrical components of the mandrel 132 so they are not identical as shown in FIG. 26. A larger sized mandrel cylinder will result in the formation of a larger trunk component leg 109, 113. This would typically also include shifting the location of the slits 135 so that the plane of blade insertion will line up with the troughs. It will be appreciated that the trifurcated arrangement is achieved by a three-component mandrel and three slits and blades that are 120° apart. Similarly, a four-branched structure would include four of each features, spaced 90° apart.

In a preferred arrangement for this embodiment, the thus deformed braided tubular supportive component is chemically and heat processed in order to set the desired diameter and mechanical properties of the main body. Once this flexible metallic stent with conformed shape is thus prepared, it is preferably lined as discussed elsewhere herein. It will be noted that the illustrated tubular braided mesh has a main cross-sectional area and has an outward flair at both ends. The braided structure is advantageously accommodated by the serrated structure of the blade edges 138, 139 in that the wire elements of the braid are grasped and secured at the ends of the bifurcation.

The expandable supportive graft of the present invention is capable of being tailored to meet specific needs, depending upon the particular defect or disease being addressed, such as occlusion, stenosis, aneurysm, arteriovenosis fistula, trauma and the like, as well as upon the anatomy of the vessel. For example, it can be desirable to have the support component of the expandable supportive graft at locations other than throughout the entirety of the graft as specifically illustrated in FIGS. 1 through 4 hereof. The bifurcated graft of FIGS. 7 and 8 shows some separation along the support component, such as between the trunk 61 and the branches 62, 63. It is also possible, with the grafts in accordance with the present invention, to provide an expandable graft having its supportive property emanating from one or more support components, while thereby providing an adjoining graft cylindrical portion which is supported primarily by its close proximity to a support component which can be presented at one end, both ends, or spaced along the expandable supportive graft in accordance with invention.

Such a structure is generally illustrated in FIG. 5, wherein an adjoining graft cylindrical portion 71 is positioned between a first support component 72 and another or second support component 73. The expandable supportive graft in accordance with the present invention provides the tailorability advantage of being able to vary within a single graft the configuration, structure and properties of the support component or components of the graft. These various properties allow the expandable supportive graft to be tailored in accordance with particular needs of the disease, defect or damage being treated. For example, support may be particularly desirable at one location being treated, while a less rigid supportive area is needed at another, generally adjoining location. By the expandable supportive graft in accordance with this invention, a single graft can be deployed in order to effect two or more different functions. By achieving multiple support and/or repair functions with a single device, possible trauma to the patient is minimized by reducing the number of transluminal passages needed to address a situation that could otherwise require separate stents or grafts, each of which is separately deployed or implanted.

With further reference to the tailorability aspects, the present invention reduces the risk of compromising the patency of the passageways being treated. This is particularly true in treating lesions at or near vascular bifurcations, branches and/or anastomoses. Typical difficulties which can be avoided by the present invention include displacing of diseased tissue, vessel spasm, dissection with or without intimal flaps, thrombosis, embolism, and the like. Another suitable use is for dilating and/or supporting vascular graft bifurcations and the like. Additionally, lesions affecting vascular trifurcations can be treated. Also treatable are obstructed openings characterized by exaggerated cicatrization, abnormal cellular growth (subintimal fibromuscular hyperplasia and the like) or arterial or venous stenosis. Moreover, these supportive grafts can be used to reinforce vascular walls, weakened by pathological processes, for example, by dissection, as in the case of aneurysms. The grafts can also obliterate congenital or acquired arteriovenous communications, and they can be applied in intrahepatic portal-caval shunts. The grafts also can maintain biological pathways open, such as the digestive, biliary, pancreatic and urinary tracts, and they help to limit the intraluminal growth of pathological processes such as fibrosis or cancer.

EXAMPLE I

This example illustrates the formation of a branched expandable supportive endoluminal graft having an expanded internal diameter of 10 mm and which is bifurcated to accommodate two endoluminal supportive graft legs of 5 to 7 mm in diameter. A liner of non-woven polycarbonate urethane (Corethane®) was spun by winding over a mandrel, generally in accordance with U.S. Pat. No. 4,475,972. In this instance, the liner consisted of approximately 400 layers of fibers. A bifurcated braided mesh tubular supportive component made in a fixture as illustrated in FIG. 26 was spray coated using a dilute solution of polycarbonate urethane having a hardness grade and a melting point lower than that used to spin the liner. It was allowed to dry with warm air. Several spray coats allow for the formation of an adhesive layer.

The previously prepared polycarbonate urethane liner was cut to length and placed inside the adhesive-coated bifurcated braided mesh and seated to closely fit the bifurcated braided mesh. A mandrel having a shape similar to the inner configuration of the bifurcated mesh was inserted from one end to act as a support. Shrink tubing was slipped over portions of this assembly. This assembly was heated to the melting point of the polycarbonate urethane adhesive while allowing the shrink tubing to heat shrink and compress the braided mesh against the liner which is supported by the shaped mandrel. After cooling, the shrink tubing was removed and the mandrel slipped out, leaving a completed trunk component as described herein.

The two endoluminal tubular expandable supportive graft leg components are prepared in accordance with a similar procedure which is simpler because of the cylindrical shape of these components.

EXAMPLE II

The procedure of Example I is substantially repeated, except the liner is a double tricot polyester mesh net. In a similar arrangement, a trunk component of the same structure was formed, except prior to insertion of the supporting mandrel, a second, innermost liner of polycarbonate urethane is positioned in order to provide a double-lined branched component.

EXAMPLE III

The procedures of Example I and of Example II are generally followed, except here the expanded inner diameter of the trunk component is 25 mm, and the cylindrical leg endoluminal grafts are 12–15 mm in diameter.

EXAMPLE IV

A branched vascular expandable supportive endoluminal graft was made using a 16 mm diameter, 12 cm long Wallstent® device as the support component in the following manner. A grounded 16 mm mandrel was rotated on a spinning machine at 500 RPM, and a spinnerette with 30 orifices was reciprocated along the axis of the mandrel at 13.8 inches/second while applying 40,000 volts to the spinnerette. Polycarbonate urethane, in dimethyl acetamide solution (45% solids) was extruded from the spinnerette at 0.123 ml/min, the fibers coming onto the mandrel in random fashion to form a mat-like structure having randomly shaped pores. The environment in the spinning chamber was controlled such that sufficient solvent from the urethane solution evaporated off during spinning to enable the fibers to be bond to underlying fibers during each transverse of the spinnerette. After 300 passes of the spinnerette, the spinning procedure was stopped and the mandrel with the spun polycarbonate urethane mat was removed from the machine and cured at 110° C. for 16 hours. The tubular mat still on the mandrel was trimmed to the appropriate size and the Wallstent® device was sheathed over the mesh and the ends taped down. Another 10 passes of polycarbonate urethane were spun over the Wallstent® device, and the fibers, while still wet, are immediately pressed through the interstices of the Wallstent® device with a silicone rubber sponge at selected longitudinal locations, such that the fibers bond to the underlying fibers of the urethane mat, thereby capturing the Wallstent® device within the urethane wall along those longitudinal locations. The assembly is then cured for an additional 3 hours at 110° C., after which the assembly is removed from the mandrel. The expandable supportive endoluminal graft formed in this manner had the bulk of the urethane mesh on the inside of the stent. The longitudinal locations which are not secured to the stent are joined together to form a seam to define two legs as generally shown in FIG. 31.

EXAMPLE V

A branched aortic expandable supportive endoluminal graft is made in the following manner. An aortic trunk supportive endoluminal graft is fabricated using a 16 mm diameter, 12 cm long support component. First, a 16 mm mandrel is rotated on a spinning machine at 500 rpm, and a spinnerette with 30 orifices reciprocated along the axis of the mandrel at 13.8 inches/second. Polycarbonate urethane, in dimethyl acetamide solution (45% solids) is extruded from the spinnerette at 0.123 ml/min and wound onto the rotating mandrel such that the fibers form a 50° pitch angle in relation to the axis of the mandrel. The environment in the spinning chamber is controlled such that sufficient solvent from the urethane solution evaporates off during spinning to enable the fibers to bond to underlying fibers during each transverse of the spinnerette. The formed spun polycarbonate urethane mesh has a length of about 16 cm, is removed from the machine and is cured at 110° C. for 16 hours. The support component is sheathed over the mesh still on the mandrel. Another 10 passes of polycarbonate urethane are spun over the tubular mesh, support component, but not over the 4 cm excess length of the internal tubular mesh, and the fibers, while still wet, are immediately pressed through the interstices of the support component with a silicone rubber sponge, such that the fibers bonded to the underlying fibers of the urethane mesh, thereby capturing the support component within the urethane wall. The assembly is then cured for an additional 3 hours at 110° C., after which the assembly is removed from the mandrel. The supportive endoluminal graft formed in this manner has fiber diameters of 10 to 20μ and pore sizes ranging from 10 to 60μ.

The length of the tubular mesh which is spaced about 4 cm from each side of the assembled endoprosthesis is then slit and sewn down the center such that the tube is branched into two smaller tubes along about 8 cm of the longitudinal central length of the tubular mesh.

The aortic trunk endoprosthesis is pulled down and sheathed on an introducer catheter, maneuvered into the aorta of a dog, via the dog's femoral artery for deployment in the abdominal aorta. Two smaller stents, of 8 mm diameter, are also pulled down onto introducer catheters and maneuvered, through each femoral artery for deployment into the seam-defined two smaller tubes or "legs" of the aortic trunk. The resultant branched endoprosthesis is for limiting further dilation of an abdominal-iliac aneurysm.

EXAMPLE VI

A branched expandable supportive endoluminal graft is provided for deployment within and repair of aorto-iliac aneurysms. A generally tubular metallic stent of the self-expandable type is adhered to the outside of a porous spun liner as follows. The graft is wound or spun from filaments deposited onto a rotating mandrel in order to form a cylindrical graft having crossing strands generally adhered together. The resulting inner liner, after it is dried, has a stent component placed over it. Then, an area of the stent is masked, such as with a piece of tape, at the location where an internal seam is to be positioned in the trunk component of the supportive endoluminal graft. The masking can take on a shape on the order of the triangular areas illustrated in FIG. 32, with the upper apex forming the upper "crotch" of the seam, and the lower apex forming the lower "crotch" of the seam. Additional fibers are then spun over the entire stent and pressed through the stent intersticies to be certain that the stent is secured to the liner. This continues until all areas of the stent are well-bonded except for the masked areas. After removal of the mandrel and of the masking material, the initially formed inner liner is free to be pinched along its length and sutured, sewed and/or glued and the like to form two distinct leg portions and a trunk portion of the liner. The resulting trunk component is as generally shown in FIGS. 31 and 32.

The leg components of the branched supportive endoluminal graft in accordance with this Example are individually made in a similar manner. The liner is formed by spinning compliant fibers over a rotating mandrel, a tubular stent component is positioned thereover and secured in place, and additional fibers are wound with the rotating mandrel. The stent is thus encapsulated between the liner fibers and the cover fibers, preferably with the aid of a soft roller or sponge to force the cover strands into the intersticies of the stent component and securement to the underlying liner fibers. After removal from the mandrel, the resulting tubular supported graft component, suitable for use as both the iliac components, is trimmed to proper length.

EXAMPLE VII

A branched aortic expandable supportive endoluminal graft was made using a liner of polycarbonate urethane. The cylindrical liner was flattened, and a longitudinal seam was formed by heat sealing together the flattened opposing portions along a thus formed seal line. A self-expanding cylindrical stent-like support component was coated on at least its inside surface with a heat-activated adhesive. The seamed liner was inserted into the stent-like support component, and the liner was inflated until the two non-seamed portions of the liner and the radially extending portions of the seamed portion of the liner engaged the inner surface of the support component. Then, this assembly with the inflated liner was placed into an oven to activate the adhesive whereby, upon subsequent cooling, the seamed liner was secured to the support component to form a branched trunk component as shown in FIGS. 31 and 32. In this example, the inflation of the liner was carried out by packing the seamed liner with salt crystals so the liner stretches in place and until adhesion between the liner and the support component had occurred.

EXAMPLE VIII

A branched trunk component is prepared as described in Example VII, except the liner inflation is carried out by expanding balloon activity, and the seam is formed by suturing. Because the branched trunk component will elongate when collapsed for entry into the delivery tool, the suturing allows for longitudinal expansion and contraction back down to the as-manufactured seam length. Such suturing is achieved by using a zig-zag stitch pattern.

EXAMPLE IX

Another branched trunk component is made as described in Example VIII, except the liner inflation is carried out by a mandrel, and the sutured seam is formed with a polyurethane compliant suture material.

It will be understood that the embodiments of the present invention which have been described are illustrative of some of the applications of the principles of the present invention. Various modifications may be made by those skilled in the art without departing from the true spirit and scope of the invention.

I claim:

1. A multiple-component branched expandable supportive endoluminal graft comprising:

a plurality of expandable supportive endoluminal components which are deployed individually at a selected location within a body vessel, each said supportive endoluminal graft component being radially compressible for endoluminal insertion and radially expandable for deployment at a desired location within a body vessel;

one of said expandable supportive endoluminal components is a trunk component, said trunk component including a tubular supporting member and a trunk liner positioned along said tubular supporting member, said trunk liner having a generally cylindrical upper body portion, at least two leg portions, and a generally cylindrical lower body portion, each said leg portion defining a leg opening into said upper body portion and another leg opening into said lower body portion;

at least one other of said expandable supportive endoluminal components is a generally cylindrical supportive leg component; and said generally cylindrical supportive leg component and one of said leg portions of the trunk component, when said leg component and trunk component are deployed within the body vessel, are telescopically positioned with respect to each other.

2. The supportive endoluminal graft in accordance with claim 1, wherein said generally cylindrical supportive leg component has an end portion which, when deployed, is positioned within one said leg opening of the trunk component.

3. The supportive endoluminal graft in accordance with claim 1, wherein said plurality of expandable supportive endoluminal components are self-expanding.

4. The supportive endoluminal graft in accordance with claim 1, wherein said plurality of expandable supportive endoluminal components are deployed by a radially expandable device.

5. The supportive endoluminal graft in accordance with claim 1, wherein said generally cylindrical supportive component includes a generally cylindrical supporting member and a generally cylindrical liner secured therealong.

6. The supportive endoluminal graft in accordance with claim 1, wherein said trunk liner is a stretchable wall of essentially inert biocompatible material, said stretchable wall being attached to a portion of the internal surface of the trunk component tubular supporting member, said stretchable wall having a diameter size that expands with said trunk component tubular supporting member.

7. The supportive endoluminal graft in accordance with claim 5, wherein said liner of the generally cylindrical supportive leg component is a stretchable wall of essentially inert biocompatible material, said stretchable wall being applied onto at least the internal surface of the generally cylindrical tubular supporting member of the leg component.

8. The supportive endoluminal graft in accordance with claim 1, wherein said at least two leg portions of the trunk liner are partially defined by a longitudinal seam which extends generally between said generally cylindrical upper and lower body portions of the trunk liner.

9. The supportive endoluminal graft in accordance with claim 8, wherein said leg portions are further defined by portions of the trunk liner which are secured to the tubular supporting member at a location spaced radially from said longitudinal seam.

10. The supportive endoluminal graft in accordance with claim 1, wherein said leg portions of the trunk liner are longitudinally generally coextensive with a central longitudinal portion of said tubular supporting member of the trunk component.

11. The supportive endoluminal graft in accordance with claim 10, wherein an outside section of each of said leg portions of the trunk liner is secured to said tubular supporting member, while inside sections of each of said leg portions are secured to each other along an internal seam.

12. The supportive endoluminal graft in accordance with claim 1, wherein said generally cylindrical supportive leg component, when deployed, is telescopically slidably positioned within one of said leg portions of the trunk component.

13. The supportive endoluminal graft in accordance with claim 5, wherein said liner of the leg component and said trunk liner are each a stretchable wall made from a porous elastomeric material that provides a structure which allows normal cellular invasion thereinto from the body vessel when implanted therewithin.

14. The supportive endoluminal graft in accordance with claim 13, wherein said porous elastomeric material of each stretchable wall is an elastomeric polymer.

15. The supportive endoluminal graft in accordance with claim 13, wherein said porous elastomeric material of said stretchable wall is a polycarbonate urethane.

16. The supportive endoluminal graft in accordance with claim 13, wherein said porous elastomeric material is coated with a thin layer of silicone rubber.

17. The supportive endoluminal graft in accordance with claim 5, wherein said trunk liner and said liner of the leg component are each a stretchable wall along the internal surface and the external surface of each tubular supporting component.

18. The supportive endoluminal graft in accordance with claim 1, wherein an exposed longitudinal end of said tubular supporting member extends longitudinally beyond and is not completely covered by said liner.

19. The supportive endoluminal graft in accordance with claim 1, wherein said tubular supporting component includes a plurality of wire strands with open areas therebetween.

20. The supportive endoluminal graft in accordance with claim 19, wherein said wire strands of the tubular supporting component are generally sinusoidally configured wire that is helically wound into the tubular supporting component, said wire defining therebetween said open areas of the tubular supporting component.

21. The supportive endoluminal graft in accordance with claim 19, wherein said wire strands of the tubular supporting component are shaped as intersecting elongated lengths integral with each other and defining said openings therebetween to form a mesh-shaped tubular supporting component.

22. The supportive endoluminal graft in accordance with claim 1, wherein said trunk component includes a projecting securement member.

23. A multiple-component branching expandable supportive endoluminal graft comprising:

a plurality of expandable supportive endoluminal graft components which are deployed individually at a selected location within a body vessel, each said supportive endoluminal graft component being radially compressible and radially expansible;

one of said expandable supportive endoluminal graft components being a trunk component having a longitudinal axis, an internal liner including a seam disposed generally along the longitudinal axis, and an external surface which is generally cylindrical and spaced outwardly from said internal liner, said trunk component having a plurality of legs defined in part by said seam, said trunk component further having two generally cylindrical body portions which flank said seam and which extend in opposite directions from said legs;

at least one other of said expandable supportive endoluminal graft components being a generally cylindrical supportive leg component;

said trunk component liner being a stretchable wall of essentially inert biocompatible material, said stretchable wall being applied onto an internal surface of a tubular supporting component; and each said leg is sized and shaped to receive said generally cylindrical supportive leg component.

24. The branching graft according to claim 23, wherein said trunk component has a network of land areas with open areas defined therebetween.

25. A method for making a multi-component bifurcating expandable supportive endoluminal graft, comprising the steps of:

providing a generally tubular self-supporting member;

providing a generally cylindrical liner made of flexible material, and flattening said liner so opposing surfaces engage each other;

forming a longitudinal seam within the thus flattened liner in order to secure opposing longitudinal portions of the liner to each other;

inserting the thus seamed liner within the generally tubular self-supporting member;

inflating the seamed liner while within the self-supporting member until radially extending surfaces of the liner engage an inner surface of the tubular self-support member; and securing said liner radially extending surfaces onto the thus engaged inner surface of the tubular self-supporting member in order to thereby assemble a branched trunk component.

26. The method of claim 25 further including providing a further expandable supportive endoluminal graft component by providing a generally cylindrical supportive leg component which is sized to be telescopically assembled with one of the leg portions of the branched trunk component.

27. The method of claim 25, wherein said inflating step includes filling the seamed liner with elutable materials.

28. The method in accordance with claim 25, wherein said inflating step includes inserting an expandable elongated tool into the seamed liner and expanding same so as to dilate the seamed liner into engagement with the self-supporting member.

29. The method in accordance with claim 25, wherein said step of forming a longitudinal seam includes applying heat along the longitudinal seam location.

30. The method in accordance with claim 25, wherein said step of forming a longitudinal seam includes suturing.

* * * * *

UNITED STATES PATENT AND TRADEMARK OFFICE
CERTIFICATE OF CORRECTION

PATENT NO. : 5,855,598
DATED : January 5, 1999
INVENTOR(S) : Leonard Pinchuk

It is certified that error appears in the above-identified patent and that said Letters Patent is hereby corrected as shown below:

```
On the title Page, under "Attorney, Agent, or Firm",
    "Fitz-Gibbon" should read --FitzGibbon--.
Col. 4, line 56, "illustrated in of" should read --illustrated in--.
Col. 11, line 14, "means an" should read --means of an--.
Col. 13, line 45, "damages branched" should read --damages to
    branched--.
Col. 14, line 51, "liner, 122c" should read --liner 122c--.
Col. 16, line 40, "with invention" should read --with the
    invention--.
```

Signed and Sealed this

Twenty-third Day of November, 1999

Attest:

Q. TODD DICKINSON

*Attesting Officer*     *Acting Commissioner of Patents and Trademarks*